United States Patent
Zhu et al.

(10) Patent No.: US 7,050,852 B2
(45) Date of Patent: May 23, 2006

(54) PACEMAKER MODE SWITCHING BASED UPON ATRIAL CONDUCTION TIME

(75) Inventors: Qingsheng Zhu, Little Canada, MN (US); Avram Scheiner, Vadnais Heights, MN (US); Julio C. Spinelli, Shoreview, MN (US); Victor T. Chen, Minnetrista, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 437 days.

(21) Appl. No.: 09/961,684

(22) Filed: Sep. 24, 2001

(65) Prior Publication Data

US 2003/0060850 A1 Mar. 27, 2003

(51) Int. Cl.
*A61N 1/362* (2006.01)

(52) U.S. Cl. ............................................ 607/9
(58) Field of Classification Search ............... 607/4, 607/9, 14, 15, 17, 25
See application file for complete search history.

(56) References Cited

U.S. PATENT DOCUMENTS

| | | | |
|---|---|---|---|
| 5,016,630 A * | 5/1991 | Moberg | 607/9 |
| 5,237,992 A * | 8/1993 | Poore | 607/18 |
| 5,342,401 A | 8/1994 | Spano et al. | 607/5 |
| 5,403,356 A | 4/1995 | Hill et al. | 607/14 |
| 5,480,413 A | 1/1996 | Greenhut et al. | 607/14 |
| 5,514,164 A | 5/1996 | Mann et al. | 607/25 |
| 5,584,867 A | 12/1996 | Limousin et al. | 607/9 |
| 5,683,429 A | 11/1997 | Mehra | 602/14 |
| 5,713,929 A | 2/1998 | Hess et al. | 607/14 |
| 5,951,593 A | 9/1999 | Lu et al. | 607/14 |
| 6,058,328 A | 5/2000 | Levine et al. | 607/14 |
| 6,144,880 A | 11/2000 | Ding et al. | 607/23 |
| 6,292,694 B1 * | 9/2001 | Schloss et al. | 607/9 |
| 6,397,105 B1 | 5/2002 | Bouhour et al. | 607/9 |
| 6,522,922 B1 * | 2/2003 | Perschbacher et al. | 607/14 |

FOREIGN PATENT DOCUMENTS

EP 1062987 * 12/2000

* cited by examiner

*Primary Examiner*—Kennedy Schaetzle
*Assistant Examiner*—Kristen Mullen
(74) *Attorney, Agent, or Firm*—Schwegman, Lundberg, Woessner & Kluth, P.A.

(57) ABSTRACT

A cardiac pacemaker is configured to estimate the intrinsic atrial conduction time from sensed signals detected by an atrial sensing channel. Atrial conduction delays have been found to be associated with the onset of atrial tachyarrhythmias. Upon detection of an atrial conduction time above a specified limit value, the pacemaker is programmed to switch from a normal pacing mode to an atrial pacing preference mode.

18 Claims, 2 Drawing Sheets

PACEMAKER MODE SWITCHING BASED UPON ATRIAL CONDUCTION TIME

FIELD OF THE INVENTION

This invention pertains to cardiac pacemakers and methods for operating such devices.

BACKGROUND

Cardiac pacemakers are medical devices, usually implantable, that provide electrical stimulation in the form of pacing pulses to selected chambers of the heart (i.e., the atrium and/or ventricle). As the term is used herein, a pacemaker is any cardiac rhythm management device that performs cardiac pacing, including implantable cardioverter/defibrillators having a pacing functionality. Pacemakers typically have a programmable electronic controller that causes the pacing pulses to be output in response to lapsed time intervals and sensed electrical activity (i.e., intrinsic heart beats not as a result of a pacing pulse). Implantable pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber by an electrode in electrical contact with the myocardium. A wave of depolarizing excitation then propagates through the myocardium, resulting in a heartbeat.

The normal rhythmic impulse of the heart is first generated in pacemaker tissue known as the sino-atrial (SA) node, spreads throughout the atria causing atrial contraction, and is then conducted to the atrioventricular (AV) node where the impulse is delayed before passing into the ventricles. The ventricles of a normal heart are then electrically stimulated by excitation emanating from the AV node that spreads to the heart via specialized conduction pathways known as Purkinje fibers. Coordinated contraction of both atria and both ventricles results in optimally filling of the ventricles with blood before they contract during systole, sometimes referred to as atrio-ventricular synchrony. If either inter-atrial or intra-atrial conduction defects exist, however, the effectiveness of the atria in acting as primer pumps for the ventricles is reduced. Such conduction defects can sometimes result from the stretching of the atrial walls that occurs in patients with congestive heart failure (CHF). It has been found that atrial conduction delays, as reflected by the duration of P-waves on a surface electrocardiogram, are a useful predictor for episodes of paroxysmal atrial fibrillation, where the atria depolarize in a chaotic fashion with no effective pumping action.

SUMMARY OF THE INVENTION

The present invention relates to a method for switching the pacing mode of a pacemaker based upon an estimate of the intrinsic atrial conduction time. A pacemaker may be programmed to pace the atria and ventricles with a normal pacing mode having specified ventricular and atrial escape intervals. The intrinsic atrial conduction time may then be estimated from atrial sense signals either by measuring the time delay between atrial sense signals generated by different atrial sensing channels with different electrode locations or by measuring the duration of a P-wave in an electrogram generated by an atrial sensing channel. If the intrinsic atrial conduction time is found to exceed a specified limit value, the pacemaker is programmed to switch the pacing mode to an atrial pacing preference mode where the atria is more preferentially paced as compared with the normal mode. Switching to the atrial pacing preference mode may include, for example, discontinuing hysteresis with respect to the atrial escape interval, shortening the atrial escape interval, and/or initiating atrial resynchronization therapy.

DETAILED DESCRIPTION

Figure 1:
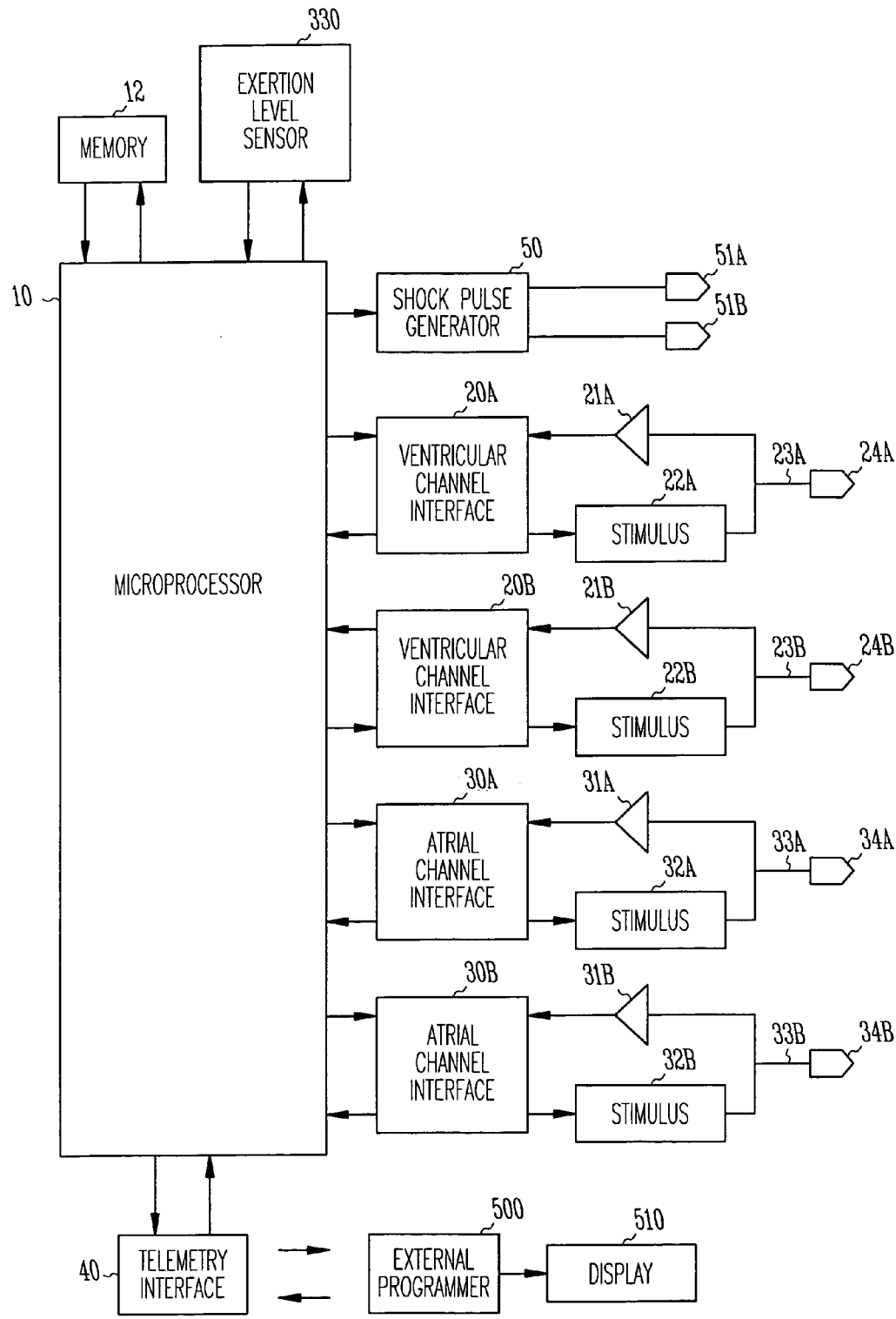
FIG. 1 is a block diagram of an exemplary cardiac rhythm management device in which may be incorporated the present invention.

In chronotropically competent patients in need of ventricular pacing, atrial triggered pacing modes are desirable because they allow the pacing to track the physiologically normal atrial rhythm, which causes cardiac output to be responsive to the metabolic needs of the body. A normal pacing mode selected for a particular patient, therefore, may pace the ventricles when triggered by an atrial sense and pace the atria on a demand basis when the atrial rate slows below a specified rate. If a measurement of the intrinsic atrial conduction time (i.e., the time it takes for the atria to depolarize during an intrinsic beat) indicates that a conduction delay exists, however, there is an increased risk of the onset of an episode of atrial fibrillation. Accordingly, it would be desirable to modify the pacing mode of the pacemaker to reduce this risk. One way of doing this is to switch the pacing mode from a normal mode to one where the atria are more likely to be paced, termed herein as an atrial pacing preference mode. Increasing the frequency of atrial pacing tends to discharge ectopic excitatory foci and interrupt re-entrant circuits responsible for fibrillation. As described below, a pacemaker can be configured to measure such atrial conduction times and switch to an atrial pacing preference mode if the atrial conduction time is above a specified limit value.

1. Pacing Modes

Most pacemakers are programmed to operate in a so-called demand mode (a.k.a., synchronous mode), where a pacing pulse is delivered to a heart chamber during a cardiac cycle only when no intrinsic beat by the chamber is detected. An escape interval is defined for each paced chamber, which is the maximum time interval in which a beat must be detected before a pace will be delivered. A ventricular escape interval thus defines the minimum rate at which the pacemaker will allow the ventricle to beat, sometimes referred to as the lower rate limit or its inverse, the lower rate interval. In a pacemaker configured to pace the atria in addition to the ventricles on a demand basis, an atrial escape interval is defined as the maximum time interval in which an atrial sense must be detected after a ventricular sense or pace before an atrial pace will be delivered. The lower rate interval in that case is the sum of the atrial escape interval and the programmed atrioventricular (AV) delay (i.e., the delay between an atrial sense or pace and a ventricular pace). If functioning properly, the pacemaker in this manner makes up for a heart's inability to pace itself at an appropriate rhythm in order to meet metabolic demand.

As pacemaker technology has developed, a number of standard operating modes have been developed which define how the device paces the heart. The modes employed for bradycardia pacing are usually described by a three-letter code developed by the Inter-Society Commission for Heart Disease where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used which implies a tracking mode), and O (for no response). A pacemaker operating in a demand mode is therefore designated with an I or a D as the third letter. Additional sensing of physiological data allows some pacemakers to change the rate at which they pace the heart in accordance with some parameter correlated to metabolic demand. Such pacemakers are called rate-adaptive and designated by a fourth letter added to the three-letter code, R.

A pacemaker operating in a demand mode may also employ hysteresis in its control algorithm to vary the escape interval. Hysteresis in this context means that if the heart starts to beat intrinsically at a rate above the lower rate limit, so that the pacemaker is not having to pace the heart, the lower rate limit is lowered to a hysteresis value. That is, the next pacing escape interval is prolonged to a hysteresis value after a spontaneous, or natural beat. The intrinsic heart rate must then fall below the hysteresis value before the pacemaker starts to pace the heart again, at which point the lower rate limit is returned to its original value. For example, the pacemaker may be programmed to pace at 60 beats per minute (bpm), but if intrinsic beats are being sensed at rates above 60 bpm, the escape interval is then lowered to a hysteresis value, e.g., 50 bpm. The advantage of hysteresis is that it enables the pacemaker to follow a natural rhythm that is just slightly below the original programmed lower rate limit (LRL) but still at a high enough rate that it is not necessary to override these natural beats with pacing. One advantage of allowing natural beats to occur to as great an extent as possible is that the longevity of the pacemaker's battery is extended due to not having to deliver as many pacing pulses. Furthermore, in a pacemaker operating in a mode that does not attempt to provide AV synchrony, such as VVI, natural beats that do provide such synchrony are physiologically better for the patient, and hysteresis provides a means of allowing such natural beats to occur as often as possible. Even in dual chamber pacemakers operating in a mode that does attempt to provide AV synchrony with atrial tracking, such as DDD or VDD, hysteresis with respect to the atrial escape interval enables increased tracking of natural atrial beats which is physiologically desirable in a chronotropically competent patient. Even in a pacemaker providing atrioventricular sequential pacing (i.e., in DDI or DVI modes) which does not track natural atrial beats, it remains desirable to maximize the number of natural beats in a patient without AV block so as to maximize the number cardiac cycles where the heart is permitted to beat with its own natural AV synchrony.

Cardiac resynchronization therapy is pacing stimulation applied to one or more heart chambers in a manner that restores or maintains synchronized bilateral contractions of the atria and/or ventricles in patients with conduction abnormalities and thereby improves pumping efficiency. Resynchronization pacing may involve pacing both ventricles and/or both atria in accordance with a synchronized pacing mode. In one implementation of bilateral synchronized pacing, which may be either biatrial or biventricular synchronized pacing, one heart chamber is designated as a rate chamber while the heart chamber contralateral to the rate chamber is designated as a synchronized chamber. For example, the right atrium may be designated as the rate atrium and the left atrium designated as the synchronized atrium. The synchronized chamber is then paced in a timed relation to a pace or sense occurring in the contralateral rate chamber. One synchronized pacing mode may be termed offset synchronized pacing. In this mode, the synchronized chamber is paced with a positive, negative, or zero timing offset as measured from a pace delivered to its paired rate chamber, referred to as the synchronized chamber offset interval. The offset interval may be zero in order to pace both chambers simultaneously, positive in order to pace the synchronized chamber after the rate chamber, or negative to pace the synchronized chamber before the rate chamber. Another synchronized mode is triggered synchronized pacing. In one type of triggered synchronized pacing, the synchronized chamber is paced after a specified trigger interval following a sense in the rate chamber, while in another type the rate chamber is paced after a specified trigger interval following a sense in the synchronized chamber. The two types may also be employed simultaneously, and triggered synchronized pacing can also be combined with offset synchronized pacing such that both chambers are paced with the specified offset interval if no intrinsic activity is sensed in the rate chamber and a pace to the rate chamber is not otherwise delivered as a result of a triggering event.

2. Hardware Platform

FIG. 1 shows a system diagram of a microprocessor-based cardiac rhythm management device with pacing functionality that is suitable for delivering therapy in accordance with the invention. The device is usually implanted subcutaneously on the patient's chest, and is connected to an electrode for each paced or sensed heart chamber by leads threaded through the vessels of the upper venous system into the heart. The controller 10 of the device is a microprocessor that communicates with a memory 12 via a bidirectional data bus. The memory 12 typically comprises a ROM (read-only memory) for program storage and a RAM (random-access memory) for data storage. The operation of the controller constitutes circuits for sensing and pacing both atria and both ventricles. The device has atrial sensing and pacing channels comprising electrode 34a–b, leads 33a–b, sensing amplifiers 31a–b, pulse generators 32a–b, and atrial channel interfaces 30a–b which communicate bidirectionally with microprocessor 10. The device also has ventricular sensing and pacing channels for both ventricles comprising electrodes 24a–b, leads 23a–b, sensing amplifiers 21a–b, pulse generators 22a–b, and ventricular channel interfaces 20a–b. In the figure, "a" designates one ventricular or atrial channel and "b" designates the channel for the contralateral chamber. In this embodiment, a single electrode is used for sensing and pacing in each channel, known as a unipolar lead. Other embodiments may employ bipolar leads that include two electrodes for outputting a pacing pulse and/or sensing intrinsic activity. Detection of depolarization by a sensing electrode results in the generation of a sense signal that can either be recorded as an electrogram or deemed to be a ventricular or atrial sense if the signal exceeds a specified threshold value. The channel interfaces 20a–b and 30a–b include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

An exertion level sensor 330 (e.g., an accelerometer or a minute ventilation sensor) is also provided in the device of FIG. 1 that enables the controller to adapt the pacing rate in accordance with changes in the patient's physical activity. A telemetry interface 40 allows for communicating with an external programmer 500 that has an associated display 510. The device of FIG. 1 may be programmed to deliver anti-tachycardia pacing and is also configured to deliver cardioversion/defibrillation shocks.

A shock pulse generator 50 is interfaced to the microprocessor for delivering shock pulses via a pair of shock electrodes 51a and 51b placed in proximity to regions of the heart. The device may have one such shock pulse generator and shock electrode pair for delivering defibrillation shocks to either the atria or the ventricles or may be capable of delivering shocks to both chambers. The sensing channels are used to both control pacing and for measuring heart rate in order to detect tachyarrythmias such as fibrillation. The device detects an atrial or ventricular tachyarrhythmia by measuring the atrial or ventricular rate, respectively, as well as possibly performing other processing on data received from the sensing channels.

3. Pacing Mode Switching

In accordance with the invention, a pacemaker is programmed to estimate the intrinsic atrial conduction time from sense signals detected by an atrial sensing channel. One way of estimating the atrial conduction time is to measure the duration of a P-wave in an electrogram generated by an atrial sensing channel or an average P-wave duration in a plurality of such electrograms generated over a period of time. Measuring the P-wave duration is best done with a unipolar atrial sensing channel so that the sensing electrode "sees" all of the depolarization occurring during an atrial contraction. Another way to estimate the atrial conduction time is by measuring the time delay between atrial sense signals generated by two atrial sensing channels with electrodes disposed in different locations. Detection of atrial depolarizations with this method may be performed using either unipolar or bipolar leads. For example, one of the atrial sensing channels of the device depicted in FIG. 1 may have its electrode disposed in the right atrium while the electrode of the other atrial sensing channel may have its electrode disposed in the coronary sinus so as to sense depolarizations occurring in the left atrium. The time delay between sensed depolarizations events in the two channels thus represents the time in which a depolarization wavefront traverses the atrium as it travels from one electrode to the other. A similar technique can be used with multiple spaced-apart electrodes where the atrial conduction time is estimated by the time difference between depolarization detection in each electrode.

When the estimated atrial conduction time exceeds a specified limit value, the pacemaker is programmed to switch from a normal pacing mode to an atrial pacing preference mode. An atrial pacing preference mode may include a shorter atrial escape interval and/or discontinuance of any hysteresis employed in the normal mode with respect to the atrial escape interval in order to increase the frequency of atrial pacing. An atrial pacing preference mode may also include atrial resynchronization pacing in order to compensate for hemodynamic effects brought about by the atrial conduction delays. Such atrial resynchronization pacing may be, for example, a triggered resynchronization mode where a sense in one atrium triggers a pace in the other, or an offset resynchronization mode where the atria are paced sequentially separated by a specified offset.

Figure 2:
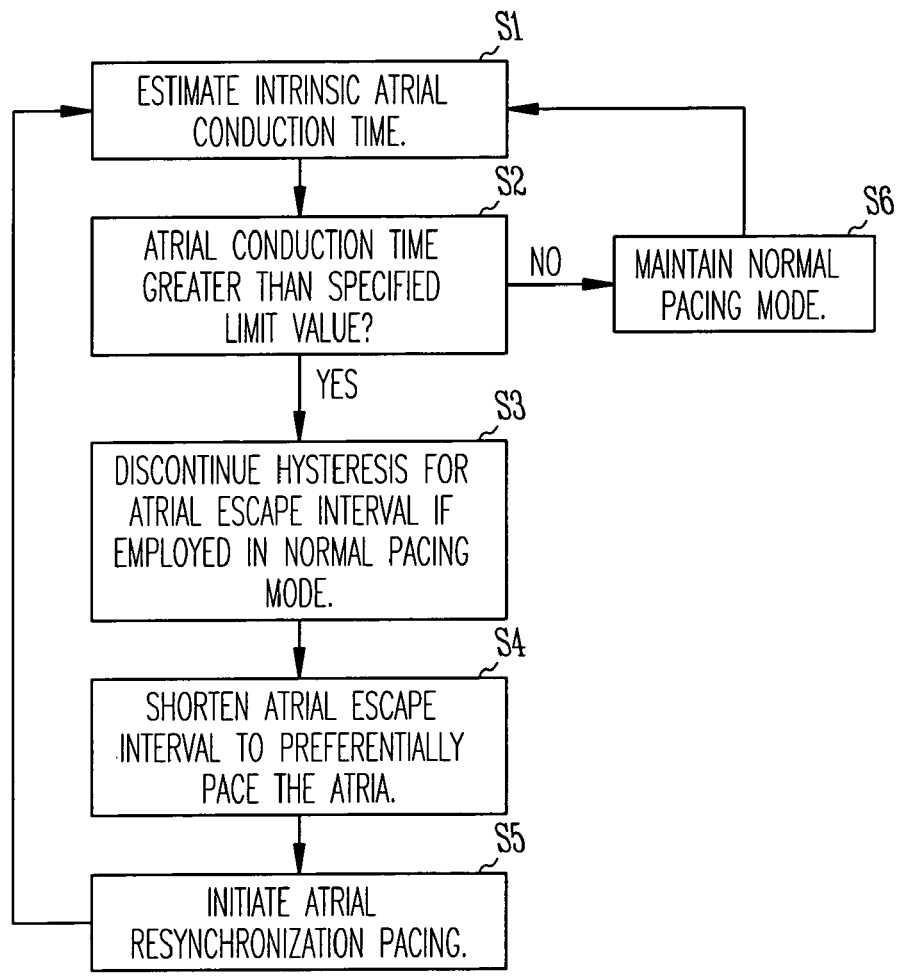
FIG. 2 is a flowchart illustrating an exemplary implementation of pacing mode switching.

In one embodiment, for example, the pacemaker is programmed to operate normally in a DDD pacing mode such that an atrial pace is delivered following a ventricular sense or pace if an atrial or ventricular sense is not detected within an atrial escape interval following the ventricular sense or pace, and a ventricular pace is delivered following an atrial sense or pace if a ventricular sense is not detected within a specified atrio-ventricular interval following the atrial sense or pace. The normal mode also incorporates hysteresis with respect to the atrial escape interval by raising the atrial escape interval to a hysteresis value following an atrial sense and returning it to a programmed value when an atrial pace is delivered. FIG. 2 illustrates the steps involved in mode switching in an exemplary implementation. At step S1 the pacemaker estimates the atrial conduction time and compares it to a specified limit value at step S2. If the atrial conduction time does not exceed the limit value, the pacemaker is returned the normal pacing mode at step S6 (or the pacing mode is left unchanged if already in the normal pacing mode). If the atrial conduction time does exceed the limit value, the pacing mode is switched to an atrial pacing preference mode by, in alternative embodiments, performing one or more of steps S3 through S5. At step S3, hysteresis with respect to the atrial escape interval is discontinued, and the atrial escape interval is shortened at step S4. Both of these mode switches result in more frequent pacing of the atria. Finally, at step S6, resynchronization pacing of the atria is initiated.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac pacemaker, comprising:
   generating atrial sense signals with one or more atrial sensing channels;
   pacing an atrium in accordance with a normal pacing mode having a specified atrial escape intervals, wherein the normal pacing mode includes raising the atrial escape interval to a hysteresis value following an atrial sense, the escape interval remaining at the hysteresis value until an atrial pace is delivered;
   estimating an intrinsic atrial conduction time based upon one or more atrial sense signals during the normal pacing mode while hysteresis of the atrial escape interval is operative;
   comparing the estimated atrial conduction time with a specified limit value;
   switching from the normal pacing mode to an atrial pacing preference mode if the estimated atrial conduction time exceeds the specified limit value, wherein the atrial pacing preference mode includes discontinuing hysteresis with respect to the atrial escape interval.

2. The method of claim 1 wherein switching to the atrial pacing preference mode includes shortening the atrial escape interval.

3. The method of claim 1 wherein switching to the atrial pacing preference mode includes adjusting an atrio-ventricular interval that defines the interval between an atrial sense or pace and a ventricular pace.

4. The method of claim 1 wherein the atrial pacing preference mode includes resynchronization pacing of the atria.

5. The method of claim 1 wherein the atrial pacing preference mode includes a triggered atrial resynchronization pacing mode.

6. The method of claim 1 wherein the atrial pacing preference mode includes an offset atrial resynchronization pacing mode.

7. The method of claim 1 wherein the atrial conduction time is estimated by measuring the duration of a P-wave in an electrogram generated by the atrial sensing channel.

8. The method of claim 1 wherein the atrial conduction time is estimated by measuring the average duration of P-waves in a plurality of electrograms generated by the atrial sensing channel.

9. The method of claim 1 wherein the atrial conduction time is estimated by measuring the time delay between atrial sense signals generated by two or more atrial sensing channels.

10. A cardiac pacemaker, comprising:
   one or more atrial sensing channels, each such channel comprising an electrode for disposing near a chamber of the heart and a sense amplifier for detecting depolarizations and generating sense signals in accordance therewith;
   an atrial pacing channel comprising a pulse generator for outputting pacing pulses to an electrode disposed near an atrium;
   a controller for controlling the operation of the pulse generators in response to sensed events and lapsed time intervals and in accordance with a programmed pacing mode; and,
   wherein the controller is programmed to:
   pace an atrium in accordance with a normal pacing mode having a specified atrial escape intervals, wherein the normal pacing mode includes raising the atrial escape interval to a hysteresis value following an atrial sense, the escape interval remaining at the hysteresis value until an atrial pace is delivered;
   estimate an intrinsic atrial conduction time based upon one or more atrial sense signals during the normal pacing mode while hysteresis of the atrial escape interval is operative;
   compare the estimated atrial conduction time with a specified limit value; and,
   switch from the normal pacing mode to an atrial pacing preference mode if the estimated atrial conduction time exceeds the specified limit value, wherein the atrial pacing preference mode includes discontinuing hysteresis with respect to the atrial escape interval.

11. The pacemaker of claim 10 wherein switching to the atrial pacing preference mode includes shortening the atrial escape interval.

12. The pacemaker of claim 10 wherein switching to the atrial pacing preference mode includes adjusting an atrio-ventricular interval that defines the interval between an atrial sense or pace and a ventricular pace.

13. The pacemaker of claim 10 wherein the atrial pacing preference mode includes resynchronization pacing of the atria.

14. The pacemaker of claim 10 wherein the atrial pacing preference mode includes a triggered atrial resynchronization pacing mode.

15. The pacemaker of claim 10 wherein the atrial pacing preference mode includes an offset atrial resynchronization pacing mode.

16. The pacemaker of claim 10 wherein the atrial conduction time is estimated by measuring the duration of a P-wave in an electrogram generated by the atrial sensing channel.

17. The pacemaker of claim 10 wherein the atrial conduction time is estimated by measuring the average duration of P-waves in a plurality of electrograms generated by the atrial sensing channel.

18. The pacemaker of claim 10 wherein the atrial conduction time is estimated by measuring the time delay between atrial sense signals generated by two or more atrial sensing channels.

* * * * *

UNITED STATES PATENT AND TRADEMARK OFFICE
CERTIFICATE OF CORRECTION

PATENT NO.        : 7,050,852 B2                                      Page 1 of 1
APPLICATION NO.   : 09/961684
DATED             : May 23, 2006
INVENTOR(S)       : Zhu et al.

It is certified that error appears in the above-identified patent and that said Letters Patent is hereby corrected as shown below:

On the face page, in field Item (75), in "Inventors", in column 1, line 5, delete "Minnetrista," and insert -- Minneapolis, --, therefor.

On the face page, in field Item (56) under "Foreign Patent Documents", in column 2, line 1, after "12/2000" insert -- A61N/1/39 --.

In column 6, line 45, in Claim 1, delete "intervals," and insert -- interval, --, therefor.

In column 7, line 37, in Claim 10, delete "intervals," and insert -- interval, --, therefor.

Signed and Sealed this

Nineteenth Day of December, 2006

JON W. DUDAS
*Director of the United States Patent and Trademark Office*